United States Patent [19]
Dondio et al.

[11] Patent Number: 5,981,540
[45] Date of Patent: Nov. 9, 1999

[54] HETEROCYCLE-CONDENSED MORPHINOID DERIVATIVES

[75] Inventors: Giulio Dondio; Silvano Ronzoni, both of Milan, Italy

[73] Assignee: SmithKline Beecham Farmaceutici S.P.A., Milan, Italy

[21] Appl. No.: 08/776,134

[22] PCT Filed: Jul. 7, 1995

[86] PCT No.: PCT/EP95/02694

§ 371 Date: Apr. 24, 1997

§ 102(e) Date: Apr. 24, 1997

[87] PCT Pub. No.: WO96/02545

PCT Pub. Date: Feb. 1, 1996

[30] Foreign Application Priority Data

Jul. 14, 1994 [IT] Italy .................. MI94A1463

[51] Int. Cl.$^6$ .............. A61K 31/44; A61K 31/535; C07D 471/22; C07D 491/22
[52] U.S. Cl. .............. 514/279; 514/232.8; 514/281; 544/125; 546/39; 546/40; 546/43; 546/44
[58] Field of Search .............. 514/279, 232.8, 514/281; 546/40, 44, 39, 43; 544/125

[56] References Cited

U.S. PATENT DOCUMENTS

| | | | |
|---|---|---|---|
| 5,223,507 | 6/1993 | Dappen et al. | 514/279 |
| 5,225,417 | 7/1993 | Dappen et al. | 514/279 |

OTHER PUBLICATIONS

Portoghese et al. (I) Jour. Med. Chem vol. 31 pp. 281–282, 1988.
Portoghese et al (II) Jour. Med. Chem. vol. 31 pp. 1344–1347, 1988.
Dondid et al Chem Abstr vol. 127 Entry 162011 abstracting WO 97 25331, 1997.
Goerlitzer et al., Archiv Der Pharmazie, vol. 325, No. 10, pp. 629–636 (1992).

*Primary Examiner*—Richard L. Raymond
*Assistant Examiner*—Brenda Coleman
*Attorney, Agent, or Firm*—Soma G. Simon; William T. King; Charles M. Kinzig

[57] ABSTRACT

Compounds of formula (I), are selective delta opioid agonsist and antagonists, and are useful as analgesics and in treating general neurologic disorders.

10 Claims, No Drawings

HETEROCYCLE-CONDENSED MORPHINOID DERIVATIVES

This application is a National Stage Entry of PCT/EP95/02694 filed Jul. 7, 1995.

The present invention is concerned with novel morphinoid compounds, processes for their preparation and their use in medicine.

The presence of at least three populations of opioid receptors (mu, delta and kappa) is now well established and documented and all three appear to be present in the central and peripheral nervous system of many species including man (Lord J. A. H. et al., Nature 1977, 267, 495).

Activation of all three opioid receptor subtypes can lead to antinociception in animal models. In particular, studies with peptidic delta agonists have indicated that activation of the delta receptor produces antinociception in rodents, primates and can induce clinical analgesia in man (D. E. Moulin et al. Pain, 1985, 23, 213). Evidence exists that suggest a lesser propensity of delta agonists to cause the usual side-effects associated with mu and kappa activation (Galligan et al, J. Pharm. Exp. Ther., 1984, 229, 641).

U.S. Pat. No. 5,223,507 and U.S. Pat. No. 5,225,417 (G. D. Searle & Co.) disclose bicycle-condensed morphinoid compounds which are said to be delta opioid agonists having therapeutic utility as analgesics agents.

WO 94/07896 (Toray Ind. Inc.) discloses indole-condensed morphinoid compounds useful as immunosuppressants, anti-allergic and anti-inflammatory agents.

We have now discovered a novel class of substituted monoheterocycle-condensed morphinoid derivatives which are potent and selective delta opioid agonists and antagonists which may therefore be of potential therapeutic utility as analgesics, immunosuppressants to prevent rejection in organ transplant and skin graft, anti-allergic and anti-inflammatory agents, brain cell protectant, agents for treating drug and alcohol abuse, gastritis, diarrhoea, cardiovascular and respiratory diseases, cough, mental illness and epilepsy and, in general, for the treatment of those pathological conditions which customarily can be treated with agonists and antagonists of the delta opioid receptor.

According to the present invention, there is provided a compound, or, a solvate or salt thereof of formula (I):

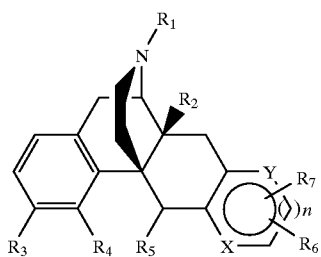

(I)

in which, $R_1$ is hydrogen, linear or branched $C_{1-6}$ alkyl, $C_{3-7}$ cycloalkyl, $C_{4-6}$ cycloalkylalkyl, $C_{3-5}$ alkenyl, aryl, aralkyl or furan-2 or 3-yl alkyl or $(CH_2)_m COR$ wherein m is 1 to 5 and R represents hydroxy, $C_{1-5}$ alkoxy, $OC_{3-6}$ alkenyl or alkylaryl or $R_1$ is a group A-B wherein A represents $C_{1-10}$ alkylene and B represents substituted or unsubstituted aryl or heteroaryl:

$R_2$ is hydrogen, hydroxy or $C_{1-5}$ alkoxy, preferably methoxy, halogen, nitro, $NR_8R_9$, $SR_8$, where $R_8$ and $R_9$, which may be the same or different are each hydrogen, $C_{1-6}$ alkyl, $COR_1$ preferably acetyl.

$R_3$ is hydrogen, hydroxy, $C_{1-5}$ alkoxy, preferably methoxy, halogen, $SR_8$, preferably hydrogen, nitro, $NHR_{10}$, $NR_{10}R_{11}$, $NHCOR_{10}$, $NHSO_2R_{10}$, where $R_{10}$ and $R_{11}$, which may be the same or different, are each hydrogen or $C_{1-6}$ alkyl, preferably methyl;

$R_4$ and $R_5$, which may be the same or different, are each independently hydrogen, hydroxy, $C_{1-5}$ alkoxy, preferably methoxy, or together may form an oxy group (—O—). $R_6$ is a group

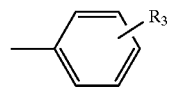

in which $R_3$ has the same meaning described above, there being up to three $R_3$ in the phenyl ring, or $R_6$ is a group $C(Z)R_{12}$, in which Z is oxygen or sulphur. $R_{12}$ is $C_{1-18}$ alkyl, $C_{1-18}$ alkoxy or $NR_{13}R_{14}$, where $R_{13}$ and $R_{14}$, which may be the same or different, are hydrogen, linear or branched $C_{1-6}$ alkyl, $C_{3-7}$ cycloalkyl, $C_{4-6}$ cycloalkylalkyl, $C_{3-6}$ alkenyl, aryl, aralkyl or an optionally substituted heterocyclic ring or may form together a $C_{3-6}$ alkyl ring which may be interrupted by an oxygen or a nitrogen.

$R_7$ is hydrogen, $C_{1-18}$ alkyl, $C_{2-18}$ alkenyl, or is a group

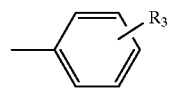

in which $R_3$ has the same meaning described above;

n is 0 or 1;

when n=0, then X and Y are independently NH, oxygen and sulphur or CH or a $R_6$- or $R_7$-substituted carbon atom; and when n=1, then X and Y are both N, or N and CH.

When $R_1$ is aryl, it is preferably phenyl and when it is aralkyl, it is preferably phenyl-$C_{1-6}$ alkyl.

Examples of $R_1$ are methyl, ethyl, propyl, allyl and cyclopropylmethyl.

Examples of $R_2$ are hydrogen and hydroxy.

Examples of $R_3$ are hydrogen, hydroxy and methoxy.

Examples of $R_4$ and $R_5$ are hydrogen, hydroxy, methoxy or together as an oxy group.

Examples of $R_6$ are COO-iPr, CONEt$_2$, CONH-i-Pr, CON(i-Pr)$_2$, CONHCH$_2$Ph, CON(—CH$_2$—)$_4$, CON(—C$_2$H$_4$OC$_2$H$_4$—), CON(i-Bu)$_2$ and CONH(CH$_2$)$_3$NEt$_2$. An example of $R_7$ is methyl.

A group of preferred compounds of formula (I) is that in which n=0, X is NH and Y is CH or a $R_6$- or $R_7$-substituted carbon atom, where $R_6$ is a group —C(Z)—$R_{12}$ where $R_{12}$ is $C_{1-6}$ alkyl, $C_{1-4}$ alkoxy or $NR_{13}R_{14}$ where $R_{13}$ and $R_{14}$ are as defined above and Z is oxygen; and $R_7$ is methyl.

Particularly preferred compounds of formula (I) are those in which $R_6$ are CONEt$_2$ and CON(i-Pr)$_2$.

The compounds of formula (I) or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in a pharmaceutical composition. In the case of salts and solvates the additional ionic and solvent moieties must also be non-toxic.

Examples of pharmaceutically acceptable salts of a compound of formula (I) include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

The compounds of formula (I) may exists in more than one stereoisomeric form, and the invention extends to all such forms as well as to their mixtures thereof, including racemates.

The compounds of formula (I), or salts or solvates thereof, may be prepared by the methods illustrated in the following general reaction schemes, or by modification thereof, using readily available starting materials, reagents and conventional synthetic procedures. If a particular enantiomer of a compound of the present invention is desired, it may be synthesised starting from the desired enantiomer of the starting material and performing reactions not involving racemization processes or it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxy, diastereomeric salts are formed with an appropriate optically active acid or base, followed by resolution of diastereomeric salts by fractional crystallization and subsequent recovery of the pure enantiomers.

Compounds (I) in which n=0, X=NH and Y is a $R_7$-substituted carbon atom, may be obtained starting from ketones of formula (II) and hydrazones of formula (III), in the presence of Zn and $CH_3COONa$ in $CH_3COOH$ as solvent (Khimiya Geterot. Soed., 1972. 342) as described in scheme 1:

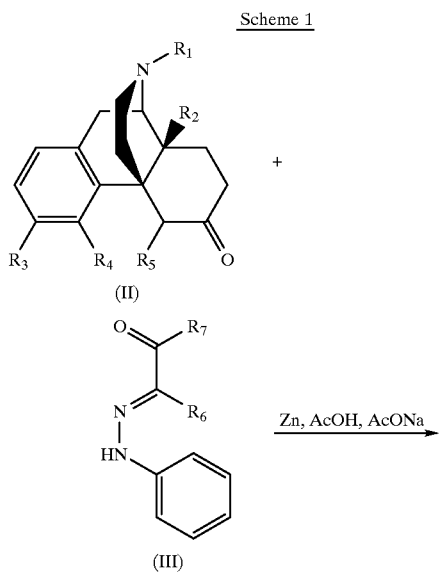

Compounds (I) in which n=0, X=NH and Y is a $R_6$-substituted carbon atom, may be obtained by cyclization of halogeno ketones of formula (IV), with ketones of formula (V) in the presence of $NH_4OH$ (Can. J. Chem., 1970, 48, 1689) as described in scheme 2:

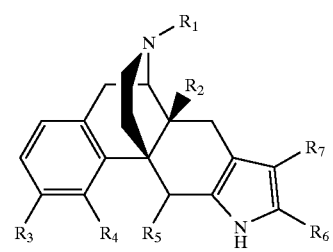

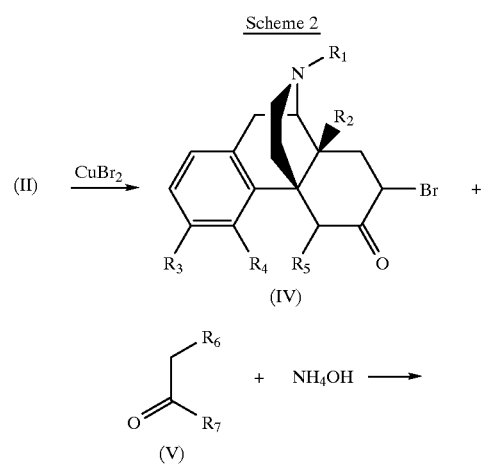

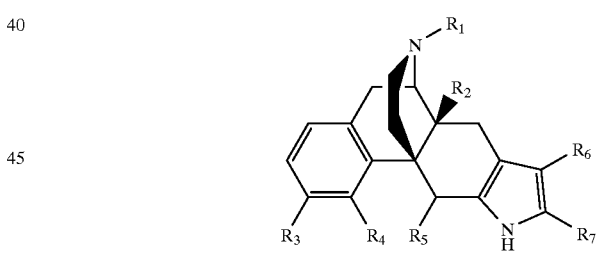

Compounds (I) in which n=0, X=O and Y is a $R_7$-substituted carbon atom, may be obtained by cyclising ketones of formula (II) with α-halogenoketones (preferably α-chloroketones) of formula (VI), in the presence of a base (J. Org. Chem., 1984, 49, 2317) as described in scheme 3:

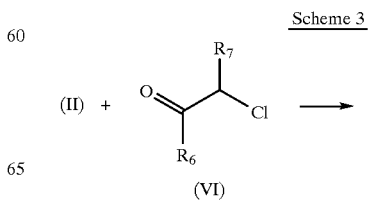

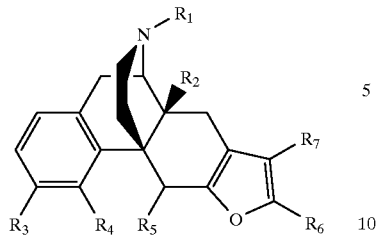

Compounds (I) in which n=0, X=O and Y is a $R_6$-substituted carbon atom, may be obtained by cyclization of the bromoketones (IV) with ketones (V) in ethanol in the presence of a base (preferably EtONa) (J. Chem. Soc. Perkin I, 1972, 372) as described in scheme 4:

Scheme 4

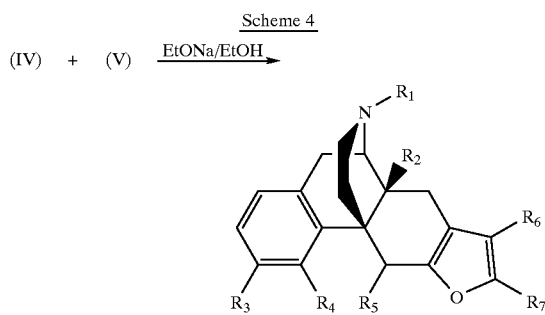

Compounds (I) in which n=0, X=S and Y is a $R_7$-substituted carbon atom, may be prepared from β-diketones of general formula (VII) (synthesised by Claisen reaction, starting from ketones (II) and esters of formula $R_7$-COOEt; J. Am. Chem. Soc., 1945, 67, 1510) and mercapto derivatives of formula (VIII) in the presence of HCl (DE 1.088.507; C.A., 1962, 56, 456) as described in scheme 5:

Scheme 5

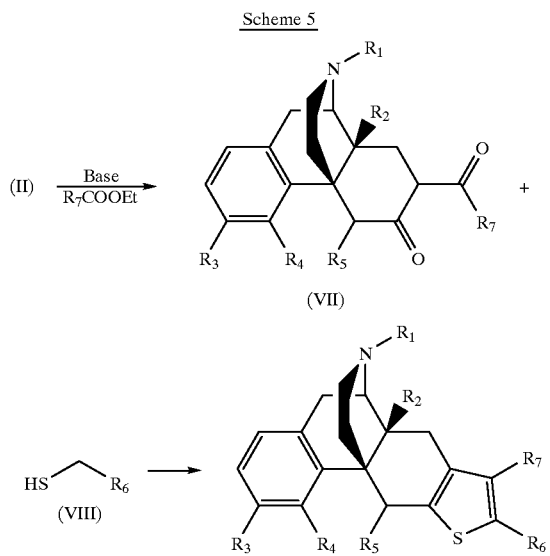

Compounds (I) in which n=0, Y=S and X is a $R_6$-substituted carbon atom, may be obtained by reacting α-mercaptoketones (IX) (which may be prepared starting from the bromoketones (IV) and $H_2S$/KOH, J. Am. Chem. Soc., 1985, 107, 4175) with an alkyne derivative of formula (X), in a solvent such as DMSO, in the presence of a base such as t-BuOK (Chem Ber., 1964, 97, 2109) as described in scheme 6:

Scheme 6

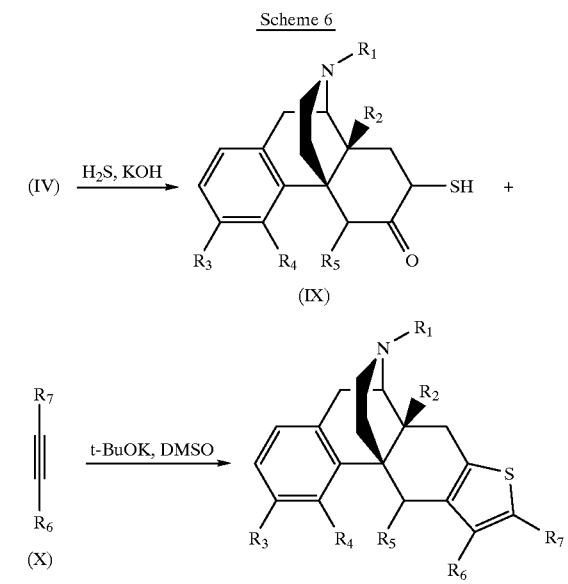

Compounds (I) in which n=0, X and Y are both N, may be obtained from hydroxyimino derivatives (XV) and $R_6$–$R_7$-substituted imidoyl chlorides of formula (XVI) in basic media, and subsequent treatment of the intermediates with $H^+$ in refluxing toluene (J. Org. Chem., 1993. 58, 7092) as described in the scheme 7:

Scheme 7

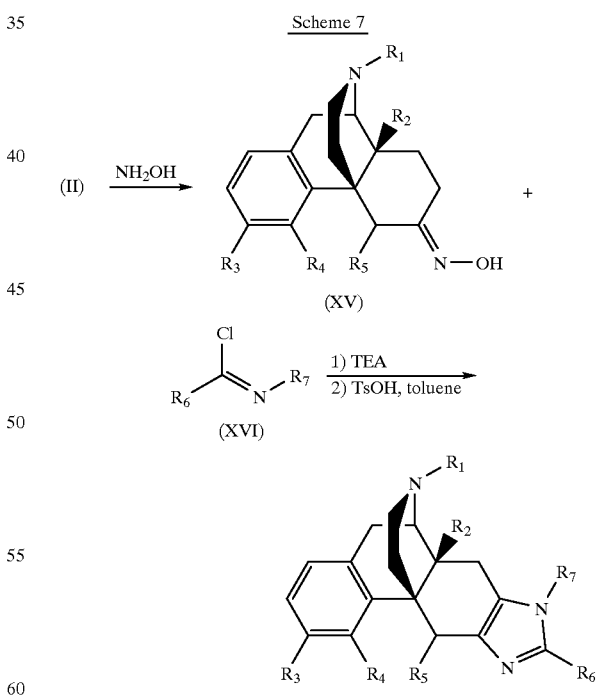

Compounds (I) in which n=1, X=N and Y=CH may be obtained by reacting α-hydroxymethylenketones (XI) (which may be prepared from ketones (II) by condensation with HCOOEt in the presence of a base; Org. Synth. Coll., 1963, 4, 536) with enamines (XII) (J. Ind. Chem. Soc., 1935, 12, 289) as described in scheme 8:

Scheme 8

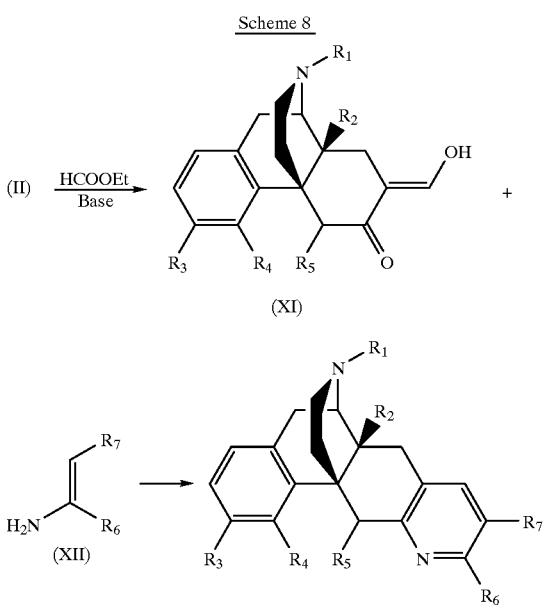

Compound (I) in which n=1, and X=Y=N may be obtained starting from α-hydroxyiminoketones (XIII) (which may be prepared from ketones (II) and i-amylnitrite/t-BuOK as described in J. Med. Chem., 1991, 34, 1715) with ethanediamines (XIV) and subsequent aromatization of the intermediate in basic media (Chem. Ber., 1967, 100, 555) as described in scheme 9:

Scheme 9

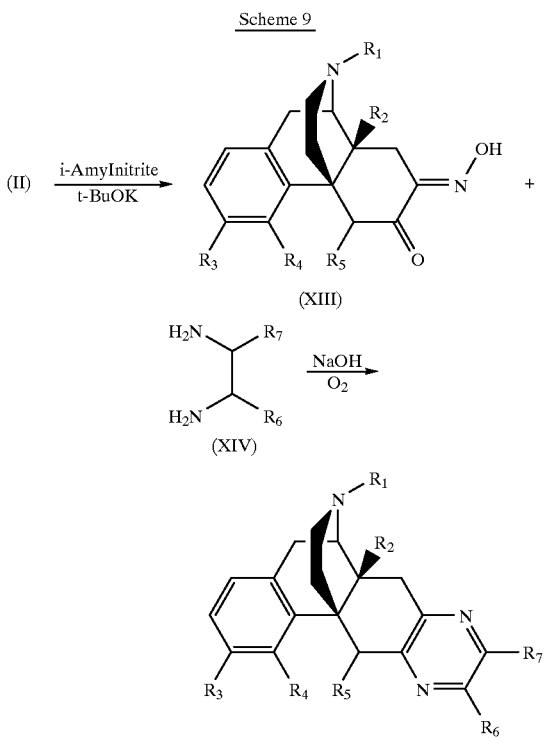

The compounds of formula (I) may be converted into their pharmaceutically acceptable salts by reaction with the appropriate organic or mineral acids.

Solvates of the compounds of formula (I) may be formed by crystallization or recrystallization from the appropriate solvent. For example, hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates. Accordingly such salts or solvates also form part of this invention.

In general compounds of formula (I) acting as selective delta receptor ligands may be useful as analgesics, immunosuppressants to prevent rejection in organ transplant and skin graft, anti-allergic and anti-inflammatory agents, brain cell protectant, for the treatment of drug and alcohol abuse, to decrease gastric secretion, for the treatment of diarrhoea, cardiovascular and respiratory diseases, cough and respiratory depression, mental illness, epileptic seizures and other neurologic disorders (herein after referred to as 'Conditions'). In particular, the activity of the compounds of formula (I) as delta agonists in standard tests indicates that they are of potential therapeutic utility as analgesic agents for the amelioration or elimination of pain.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of the Conditions.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the Conditions.

Preferably, a pharmaceutical composition of the invention is in unit dosage form and in a form adapted for use in the medical or veterinarial fields. For example, such preparations may be in a pack form accompanied by written or printed instructions for use as an agent in the treatment of the Conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia: aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

The compounds of this invention may also be administered by inhalation, via the nasal or oral routes. Such administration can be carried out with a spray formulation comprising a compound of the invention and a suitable carrier, optionally suspended in, for example, a hydrocarbon propellant.

Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilising a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg. in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

No unacceptable toxicological effects are expected with compounds of the invention when administered in accordance with the invention.

The present invention also provides a method for the treatment and/or prophylaxis of the Conditions in mammals, particularly humans, which comprises administering to the mammal in need of such treatment and/or prophylaxis an effective amount of a compound of formula (I) or a pharmaceutically acceptable salt or solvate thereof.

The activity of the compounds of the present invention as selective delta ligands is determined in radioligand binding assays as described below.

Mouse brain membranes were prepared as described by Kosteriitz (*Br. J. Pharmacol.*, 1981, 73, 939.). The binding of the preferential delta ligand [$^3$H]-[D-Ala$^2$, D-Leu$^5$]-enkephalin (DADLE) was evaluated at its $K_D$ concentration (1.3 nM) in presence of 40 nM of the unlabelled mu ligand [D-Ala$^2$, MePhe$^4$, Gly-ol$^5$]-enkephalin (DAMGO). The binding of the mu ligand [$^3$H]-DAMGO (*Eur. J. Pharmacol.*, 1989, 166, 213) and of the kappa ligand [$^3$H]-U69593 (*Excerpta Medica*, 1990, 211) were carried out at 0.5 nM. The non-specific binding was determined in presence of naloxone (10 $\mu$M) for all tritiated ligands. Binding data were expressed as percentage of inhibition and fitted the following equation: $f(x)=100 \cdot X/(IC_{50}+X)$ where X are cold drug concentration values. The $IC_{50}$ obtained were used to calculate the inhibitory constants ($K_i$) accordingly to the Cheng and Prusoff relation (*Biochem. Pharmacol.*, 1973, 22, 3099).

The delta agonist/antagonist activity of the compounds of the present invention is determined in the mouse vas deferens (MVD) bioassay as described below.

Vasa deferentia were obtained from CD-1 mice and were suspended in a Mg$^{2+}$-free Krebs buffer at 37° C. The tissues were electrically stimulated with pulse trains having the following parameters: train duration 50 ms, stimulus duration 2 ms, frequency of stimuli 50 Hz, maximal voltage 60–70 V, train frequency 0.1 Hz. Concentration response curves for each compounds were constructed cumulatively. Linear regression analysis and $IC_{50}$ concentrations were evaluated according to Tallarida and Murray (*Manual of Pharmacological Calculations*, Springer Verlag N.Y., 1981).

The most potent compounds described in the present invention showed affinities for the delta receptor ranging from 0.5 to 200 nM with delta selectivity ranging from 20 to 1500 times in respect to the other opioid receptor types. These compounds displayed also potent delta agonist or antagonist properties in the MVD preparation. Selective delta agonists (antagonised by the selective delta antagonist naltrindole) displayed $IC_{50}$s ranging from 1 to 500 nM. For example, the compound of Example 7 shows a Ki delta=1.59 nM, Ki mu/Ki delta=218 and Ki kappa/Ki delta=2259. In the MVD this compound shows an $IC_{50}$=25 nM selectively antagonised by 30 nM of NTI (10-fold shift of the dose-response curve).

Mouse abdominal constriction (MAC) (*Proc. Soc. Exp. Biol. Med.,* 1957, 95, 729), mouse tail-flick (MTF) (*J. Pharm. Exp. Ther.,* 1941, 72, 74) and mouse tail-flick warm water (MTF-WW) (*Life Sci.,* 1986, 39, 1795) were adopted to evaluate the antinociceptive efficacy of the compounds of the present invention.

The following Examples 1 to 4 illustrate the preparation of compounds of general formula (I) of the present invention. Examples 1 to 19 are summarised in the Chemical Table, Examples 5 to 19 being obtained according to the same general procedure as described in Examples 1 to 3, starting from the corresponding known ketones of general formula (II) and the corresponding known hydrazones of general formula (III).

EXAMPLE 1

[8R-(4bS*,8α,8aβ,12bβ)]-11-Diethylaminocarbonyl-7,10-dimethyl-5,6,7,8,12,12b-hexahydro-4,8-methanobenzofuro[3,2-e]pyrrolo[2,3-g]isoquinoline-1,8a-(9H)-diol hydrochloride 0.9 g (2.7 mmols) of oxymorphone hydrochloride, 2.09 g (8.1 mmols of N,N-diethyl-2-phenylhydrazono-3-oxobutyramide, were dissolved in a mixture of 15 ml of glacial acetic acid and 0.64 g (8.1 mmols) of $CH_3COONa$. The solution was heated to 60° C. then, under nitrogen atmosphere, 1.06 g (16.2 mmol) of zinc dust were added portionwise. The resulting mixture was refluxed for 2 h and cooled to room temperature. The reaction mixture was poured in ice and the pH was adjusted to 8 with 25% $NH_4OH$ and then extracted with AcOEt. The organic layer was dried over $Na_2SO_4$ and the solvent was removed in vacuo. The residue was purified by flash chromatography (AcOEt/MeOH/conc. $NH_4OH$ 80:20:0.5), dissolved in MeOH and the solution brought to acidic pH with HCl/$Et_2O$. The precipitate was filtered and recrystallized twice from EtOH to yield 0.38 g of the title compound.

EXAMPLE 2

[8R-(4bS*,8α,8aβ,12b β)]-11-Diethylaminocarbonyl-10-methyl-7-(2-propenyl)-5,6,7,8,12,12b-hexahydro-4,8-methanobenzofuro[3,2-e]pyrrolo[2,3-g]isoquinoline-1,8a-(9H)-diol hydrochloride 1.0 g (2.75 mmoles) of naloxone hydrochloride, 2.15 g (8.25 mmoles) di N,N-diethyl-2-phenylhydrazono-3-oxobutyramide, 0.68 g (8.25 mmoles) of $CH_3COONa$, 1.06 g (16.2 mmoles) of zinc dust and 15 ml of glacial acetic acid were treated as described in the Example 1. The residue was purified by flash chromatography (AcOEt/MeOH/conc. $NH_4OH$ 80:20:0.5), dissolved in MeOH and the solution brought to acidic pH with HCl/$Et_2O$. The precipitate was filtered and recrystallized twice from EtOH to yield 0.95 g of the title compound.

EXAMPLE 3

[8R-(4bS*,8α,8aβ,12bβ)]7-Cyclopropylmethyl11-diethylaminocarbonyl-10-methyl-5,6,7,8,12,12b-hexahydro-4,8-methanobenzofuro[3,2-e]pyrrolo[2,3-g]isoquinoline-1,8a-(9H)-diol hydrochloride 0.5 g (1.33 mmoles) of naltrexone hydrochloride, 1.04 g (4 mmoles) of N,N-diethyl-2-phenylhydrazono-3-oxobutyramide, 0.33 g (4 mmoles) of $CH_3COONa$, 0.783 (12 mmoles) di zinc dust and 10 ml of glacial acetic acid were treated as described in the Example 1. The residue was purified by flash chromatography (AcOEt/MeOH/conc. $NH_4OH$ 80:20:0.5), dissolved in MeOH and the solution brought to acidic pH with HCl/$Et_2O$. The precipitate was filtered and recrystallized from MeOH to yield 0.15 g of the title compound.

EXAMPLE 4

[8R-(4bS*,8α,8aβ,12bβ)]-11-Diethylaminocarbonyl-10-methyl-7-propyl-5,6,7,8,12,12b-hexahydro-4,8-methanobenzofuro[3,2-e]pyrrolo[2,3-g]isoquinoline-1,8a-(9H)-diol hydrochloride 0.57 g (1.2 mmoles) of [8R-(4bS*,8α,8aβ,12bβ)]-11-diethylaminocarbonyl-10-methyl-7-(2-propenyl)-5,6,7,8,12,12b-hexahydro-4,8-methanobenzofuro[3.2-e]pyrrolo[2,3-g]isoquinoline-1,8a-(9H)-diol hydrochloride were dissolved in 120 ml of abs. EtOH and hydrogenated over Pd/C 10% at 30 p.s.i. for 2 h at room temperature. The catalyst was filtered off and the solvent was removed in vacuo. The residue was dissolved in a mixture of MeOH/EtOH 1:1 and the solution brought to acidic pH with HCl/$Et_2O$. The precipitate was filtered and recrystallized from EtOH to yield 0.28 g of the title compound.

CHEMICAL TABLE

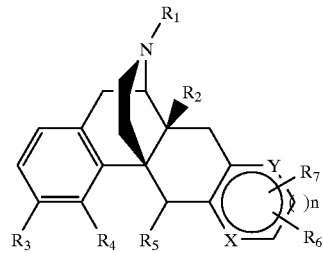

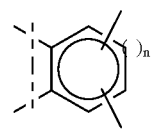

| Ex. | name | $R_1$ | $R_2$ | $R_3$ | $R_4$ | $R_5$ | | $R_6$ |
|---|---|---|---|---|---|---|---|---|
| 1 | [8R-(4bS*,8α,8aβ,12bβ)]-11-Diethylaminocarbonyl-7,10-dimethyl-5,6,7,8,12,12b-hexahydro-4,8-methanobenzofuro[3,2-e]pyrrolo[2,3-g]isoquinoline-1,8a(9H)-diol hydrochloride | Me | OH | OH | —O— | | pyrrole with $R_7$, $R_6$ | $CONEt_2$ |
| 2 | [8R-(4bS*,8α,8aβ,12bβ)]-11-Diethylaminocarbonyl-10-methyl-7-(2-propenyl)-5,6,7,8,12,12b-hexahydro-4,8-methanobenzofurol[3,2-e]pyrrolo[2,3-g]isoquinoline-1,8a(9H)-diol hydrochloride | Allyl | OH | OH | —O— | | pyrrole with $R_7$, $R_6$ | $CONEt_2$ |
| 3 | [8R-(4bS*,8α,8aβ,12bβ)]-7-Cyclopropylmethyl-11-diethylaminocarbonyl-10-methyl-5,6,7,8,12,12b-hexahydro-4,8-methanobenzofuro[3,2-e]pyrrolo[2,3-g]isoquinoline-1,8a(9H)-diol hydrochloride | CPM | OH | OH | —O— | | pyrrole with $R_7$, $R_6$ | $CONEt_2$ |
| 4 | [8R-(4bS*,8α,8aβ,12bβ)]-11-Diethylaminocarbonyl-10-methyl-7-propyl-5,6,7,8,12,12b-hexahydro-4,8-methanobenzofuro[3,2-e]pyrrolo[2,3-g]isoquinoline-1,8a(9H)-diol hydrochloride | n-Pr | OH | OH | —O— | | pyrrole with $R_7$, $R_6$ | $CONEt_2$ |
| 5 | [8R-(4bS*,8α,8aβ,12bβ)]-11-Diisopropylaminocarbonyl-7,10-dimethyl-5,6,7,8,12,12b-hexahydro-4,8-methanobenzofuro[3,2-e]pyrrolo[2,3-g]isoquinoline-1,8a(9H)-diol hydrochloride | Me | OH | OH | —O— | | pyrrole with $R_7$, $R_6$ | $CON(i\text{-}Pr)_2$ |
| 6 | [8R-(4bS*,8α,8aβ,12bβ)]-11-Benzylaminocarbonyl-7,10-dimethyl-5,6,7,8,12,12b-hexahydro-4,8-methanobenzofuro[3,2-e]pyrrolo[2,3-g]isoquinoline-1,8a(9H)-diol hydrochloride | Me | OH | OH | —O— | | pyrrole with $R_7$, $R_6$ | $CONHCH_2Ph$ |
| 7 | [8R-(4bS*,8α,8aβ,12bβ)]-11-Diethylaminocarbonyl-7,10-dimethyl-1-methoxy-5,6,7,8,12,12b-hexahyro-(9H)-4,8-methanobenzofuro[3,2-e]pyrrolo[2,3-g]isoquinoline hydrochloride | Me | H | OMe | —O— | | pyrrole with $R_7$, $R_6$ | $CONEt_2$ |

CHEMICAL TABLE

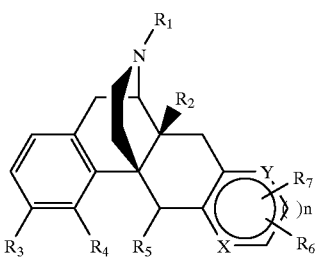

| | | R₁ | R₂ | R₃ | R₄ | R₅ | X | Y | R₆/R₇ | |
|---|---|---|---|---|---|---|---|---|---|---|
| 8 | [8R-(4bS*,8α,8aβ,12bβ)]-7,10-Dimethyl-11-pyrrolidinocarbonyl-5,6,7,8,12,12b-hexahydro-4,8-methanobenzofuro[3,2-e]pyrrolo[2,3-g]isoquinoline-1,8a(9H)-diol hydrochloride | Me | OH | OH | | —O— | | 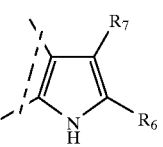 | CON(CH₂)₄ |
| 9 | [8R-(4bS*,8α,8aβ,12bβ)]-11-Diethylaminocarbonyl-7,10-dimethyl-5,6,7,8,12,12b-hexahydro-4,8-methanobenzofuro[3,2-e]pyrrolo[2,3-g]isoquinoline-1(9H)-ol hydrochloride | Me | H | OH | | —O— | | 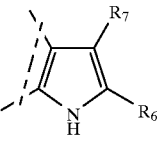 | CONEt₂ |
| 10 | [8R-(4bS*,8α,8aβ,12bβ)]-7,10-Dimethyl-11-morpholinocarbonyl-5,6,7,8,12,12b-hexahydro-4,8-methanobenzofuro[3,2-e]pyrrolo[2,3-g]isoquinoline-1,8a(9H)-diol hydrochloride | Me | OH | OH | | —O— | | 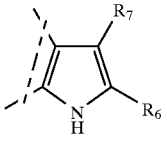 | CO[N(CH₂)₄O] |
| 11 | [10R,4bS-(4bβ,9aβ)]-7-Diisopropylaminocarbonyl-8,14-dimethyl-4-hydroxy-3-methoxy-4b,5,9,9a,10,11-hexahydro-(6H)-[2,3-h]pyrrolo[10,4b]imino ethanophenanthrene (*) | Me | H | OMe | OH | H | | 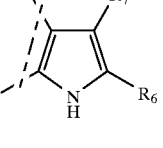 | CON(i-Pr)₂ |
| 12 | [8R-(4bS*,8α,8aβ,12bβ)]-11-Diisopropylaminocarbonyl-7,10-dimethyl-1-methoxy-5,6,7,8,12,12b-hexahydro-(9H)-4,8-methanobenzofuro[2,3-e]pyrrolo[2,3-g]isoquinoline hydrochloride | Me | H | OMe | | —O— | | 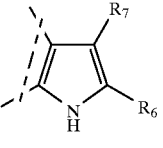 | CON(i-Pr)₂ |
| 13 | [8R-(4bS*,8α,8aβ,12bβ)]-11-Diethylaminocarbonyl-7,10-dimethyl-1-methoxy-5,6,7,8,12,12b-hexahydro-4,8-methanobenzofuro[3,2-e]pyrrolo[2,3-g]isoquinoline-8a(9H)-ol hydrochloride | Me | OH | OMe | | —O— | | 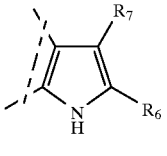 | CONEt₂ |
| 14 | [10R,4bS-(4bβ,9aβ)]-7-Diethylaminocarbonyl-8,14-dimethyl-4-hydroxy-3-methoxy-4b,5,9,9a,10,11-hexahydro-(6H)-[2,3-h]pyrrolo[10,4b]imino ethanophenanthrene (*) | Me | H | OMe | OH | H | | 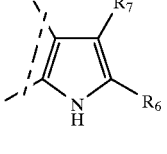 | CONEt₂ |

CHEMICAL TABLE

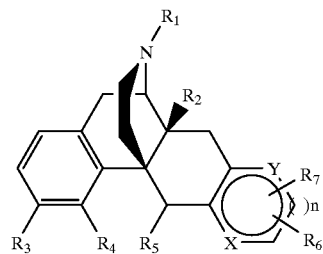

| Ex. | | R3 | R4 | R5 | X | (ring) | R6 |
|---|---|---|---|---|---|---|---|
| 15 | [8R-(4bS*,8α,8aβ,12bβ)]-11-(3-Diethylaminopropyl)aminocarbonyl-7,10-dimethyl-1-methoxy-5,6,7,8,12,12b-hexahydro-(9H)-4,8-methanobenzofuro[3,2-e]pyrrolo[2,3-g] isoquinoline dihydrochloride | Me | H | OMe | —O— | pyrrole with R7, R6 | CONH(CH2)3NEt2 |
| 16 | [8R-(4bS*,8α,8aβ,12bβ)]-11-Diethylaminocarbonyl-7,10-dimethyl-5,6,7,8,12,12b-hexahydro-(9H)-4,8-methanobenzofuro[3,2-e]pyrrolo[2,3-g] isoquinoline (*) | Me | H | H | —O— | pyrrole with R7, R6 | CONEt2 |
| 17 | [8R-(4bS*,8α,8aβ,12bβ)]-7,10-Dimethyl-1-methoxy11-(2-methylpropyl)oxycarbonyl-5,6,7,8,12,12b-hexahydro-[9H]-4,8-methanobenzofuro[3,2-e]pyrrolo[2,3-g] isoquinoline hydrochloride | Me | H | OMe | —O— | pyrrole with R7, R6 | COO-i-Bu |
| 18 | [8R-(4bS*,8α,8aβ,12bβ)]-11-Diisobutylaminocarbonyl-7,10-dimethyl-1-methoxy-5,6,7,8,12,12b-hexahydro--[9H]-4,8-methanobenzofurol[3,2-e]pyrrolo[2,3-g] isoquinoline (*) | Me | H | OMe | —O— | pyrrole with R7, R6 | CONH-iPr |
| 19 | [8R-(4bS*,8α,8aβ,12bβ)]-7,10-Dimethyl-11-isopropylaminocarbonyl-1-methoxy-5,6,7,8,12,12b-hexahydro-[9H]-4,8-methanobenzofuro[3,2-e]pyrrolo[2,3-g] isoquinoline hydrochloride | Me | H | OMe | —O— | pyrrole with R7, R6 | CONH-iPr |

| Ex. | R7 | $[\alpha]_D^{20}$ C = 0.1, MeOH | MP (°C.) | m/z | NMR |
|---|---|---|---|---|---|
| 1 | Me | −333.8 | 303 dec. | 437 (M+); EI | (DMSO): 11.20(s, 1H); 9.16(s, 1H); 9.15(s br, 1H); 6.60(ABq, 2H); 6.12(s br, 1H); 5.40(s, 1H); 3.69(d br, 1H); 3.47–3.30(m, 5H); 3.18–3.02(m, 2H); 2.86(s br, 3H); 2.75–2.65(m, 1H); 2.55–2.45(m, 1H); 2.45(d, 1H); 2.23(d, 1H); 1.82(s, 3H); 1.70(d, br); 1.02(t, 6H). |
| 2 | Me | −311.7 | 281 dec. | 464 (M+); FAB | (CDCl3): 9.15(s br, 1H); 6.67(d, 1H); 6.53(d, 1H); 5.90–5.76(m, 1H); 5.51(2, 1H); 5.26–5.15(m, 2H); 3.62–3.51(m, 2H); 3.45–3.33(m, 2H); 3.16(d, 1H); 3.14(d, 1H); 3.07(m, 1H); 2.73(dd, 1H); 2.59(d br, 1H); 2.44(d, 1H); 2.31(d, 1H); 2.28(m, 1H); 1.90(s, 3H); 1.72(m, 1H); 1.11(t, 6H). |
| 3 | Me | −358.1 | 298 dec. | 478 (MH+) FAB | (DMSO): 11.15(2, 1H); 9.12(s br, 1H); 8.90(s, 1H); 6.61(d, 1H); 6.53(d, 1H); 6.23(s br, 1H); 5.40(s, 1H); 4.03(d, 1H); 3.50–3.30(m, 5H); 3.18(dd, 1H); 3.08(d br, 1H); 2.93(m, 1H); 2.75–2.57(m, 1H); 2.58(d, 1H); 2.57(m, 2H); 2.22(d, 1H); 1.80(s, 3H); 1.62(d br, 1H); 1.07(d br, 1H); 1.06(m, 1H); 0.78–0.35(m, 4H). |
| 4 | Me | −365.1 | 306–307 | 466 (M+) FAB | (CDCl3): 9.28(s br, 1H); 6.75(d, 1H); 6.61(d, 1H); 5.60(s, 1H); 3.74–3.62(m, 2H); 3.54–3.44(m, 2H); 3.24(d, 1H); 3.13(d, 1H); 2.85(dd, 1H); 2.67(m, 1H); 2.56(m, 2H); 2.55(d, 1H); 2.41(d, 1H); 2.40(m, 2H); 1.99(s, 3H); 1.82(m, 1H); 1.69–1.57(m, 2H); 1.20(t, 6H); 1.04(t, 3H). |
| 5 | Me | −354.3 | 294 dec. | 466 (MH)+ TSP | (DMSO): 11.08(s, 1H); 9.16(s, 1H); 9.15(s br, 1H); 6.66(d, 1H); 6.58(d, 1H); 6.07(s br, 1H); 5.41(s, 1H); 3.78–3.62(m, 3H); |

-continued

CHEMICAL TABLE

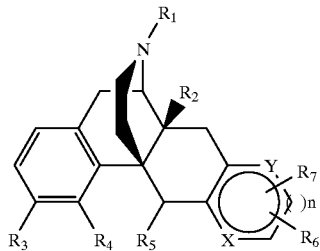

| | | | | |
|---|---|---|---|---|
| | | | | 3.39(d, 1H); 3.11(dd, 1H); 3.06(m, 1H); 2.84(s br, 3H); 2.74–2.62(m, 1H); 2.50(m, 1H); 2.47(d, 1H); 2.22(d, 1H); 1.79(s, 3H); 1.70(dd, 1H); 1.25(d, 12H). |
| 6 Me | −466.3 | >300 | 472 (MH)+ FAB | (DMSO): 11.50(s, 1H); 9.21(s, 1H); 9.20(s br, 1H); 8.21(ABX, 1H); 7.36–7.20(m, 5H); 6.67(d, 1H); 6.59(d, 1H); 6.20(s br, 1H); 5.42(s, 1H); 4.42(ABX, 2H); 3.73(d, 1H); 3.40(d, 1H); 3.14(dd, 1H); 3.08(m, 1H); 2.85(s br, 3H); 2.78–2.62(m, 1H); 2.53(d, 1H); 2.49(m, 1H); 2.21(d, 1H); 2.09(s, 3H); 1.73(dd, 1H). |
| 7 Me | −422.7 | 289–290 dec. | 436 (MH+); FAB | (DMSO): 11.50(s br, 1H); 11.20(s, 1H); 6.80(d, 1H); 6.70(d, 1H); 5.54(s, 1H); 3.95(s br, 1H); 3.72(s, 3H); 3.40–3.25(m, 4H); 3.25(d, 1H); 3.25–3.10(m, 1H); 3.06–2.88(m, 2H); 2.81(s br, 3H); 2.80–2.62(m, 1H); 2.42–2.22(m, 2H); 1.92(dd, 1H); 1.89(s, 3H); 1.66(dd, H). |
| 8 Me | −463.2 | 290 dec. | 436 (M+) FAB | (DMSO): 11.10(s, 1H); 9.11(s, 2H); 6.65(d, 1H); 6.55(d, 1H); 5.40(s, 1H); 3.62(m, 1H); 3.42(m, 4H); 3.30(m, 1H); 3.15–3.00(m, 2H); 2.80(s br, 3H); 2.50(m, 2H); 2.45(d, 1H); 2.22(d, 1H); 1.88(s, 3H); 1.81(m, 4H); 1.68(d br, 1H). |
| 9 Me | −385.9 | 273 dec. | 422 (MH+) FAB | (DMSO, base): 11.00(s, 1H); 8.82(s, 1H); 6.53(d, 1H); 6.44(d, 1H); 5.38(s, 1H); 3.40(m, 4H); 3.20(d, 1H); 2.98(d, 1H); 2.50–2.22(m, 4H); 2.29(s, 3H); 2.19(dd, 1H); 1.90(ddd, 1H); 1.79(s, 3H); 1.68(m, 2H). |
| 10 Me | −325.22 | 270–280 dec. | 451 (M+); EI | (DMSO): 11.30(s, 1H); 9.20(s, 1H); 9.16(s br, 1H); 6.62(d, 1H); 6.58(d, 1H); 6.19(s, 1H); 5.40(s, 1H); 3.70(d, 1H); 3.58(m, 4H); 3.48(m, 4H); 3.40(d, 1H); 3.12(dd, 1H); 3.08(m, 1H); 2.85(d, 3H); 2.75–2.62(m, 1H); 2.50(m, 1H); 2.48(d, 1H); 2.23(d, 1H); 1.86(s, 3H); 1.71(dd, 1H). |
| 11 Me | −121.1 | 214–216 | 465 (M+.) EI | (DMSO): 10.20(s, 1H); 8.05(s, 1H); 6.66(d, 1H); 6.51(d, 1H); 4.68(d, 1H); 3.75(m, 2H); 3.69(s, 3H); 2.91(m, 1H); 2.82(m, 2H); 2.40–2.20(m, 3H); 2.25(s, 3H); 2.08(dd, 1H); 1.95(m, 2H); 1.82(d, 1H); 1.74(s, 3H); 1.65(ddd, 1H); 1.25(d, 12H). |
| 12 Me | −378.1 | 291 dec. | 463 (M+.) EI | (DMSO): 11.10(s, 2H); 6.80(d, 1H); 6.70(d, 1H); 5.55(s, 1H); 3.97(d, 1H); 3.70(s, 3H); 3.67(m, 2H); 3.25(d, 1H); 3.22(m, 1H); 3.07–2.92(m, 2H); 2.85(d, 3H); 2.29–2.12(m, 1H); 2.40–2.20(m, 2H); 1.95(dd, 1H); 1.77(s, 3H); 1.68(dd, 1H); 1.24(d, 12H). |
| 13 Me | −358.8 | 204 dec. | 451 (M+.) EI | (DMSO): 11.20(s, 1H); 9.22(s br, 1H); 6.83(d, 1H); 6.70(d, 1H); 6.20(s, 1H); 5.49(s, 1H); 3.76(d, 1H); 3.70(s, 3H); 3.45(d, 1H); 3.37(q, 4H); 3.29(s, 3H); 3.18(dd, 1H); 3.10(m, 1H); 2.86(d br, 3H); 2.75–2.61(m, 1H); 2.55(m, 1H); 2.52(d, 1H); 2.22(d, 1H); 1.80(s, 3H); 1.73d br, 1H). |
| 14 Me | −340.5 | 234–235 | 437 (M+.); EI | (CDCl3): 8.06(s br, 1H); 7.25(s, 1H); 6.60(ABq, 2H); 5.95(s, 1H); 4.60(d, 1H); 3.79(s, 3H); 3.56(dq, 2H); 3.40(dq, 2H); 3.05(m, 1H); 3.00(d, 1H); 2.88(dd, 1H); 2.52–2.32(m, 3H); 2.41(s, 3H); 2.25–2.09(m, 3H); 1.95(ddd, 1H); 1.88(s, 3H); 1.80(ddd, 1H); 1.12(t, 6H). |
| 15 Me | −381.4 | 269–271 | 492 (M+.); EI | |
| 16 Me | −559.2 | 240–241 | 405 (M+.); EI | |
| 17 Me | −512.5 | 278–279 dec. | 436.1 (M+.); EI | |
| 18 Me | −697.6 | 141–143 | 491.0 (M+.); EI | |
| 19 Me | −475.2 | 257 dec. | 421.1 (M+.); EI | |

(*) compound transformed in the corresponding free base and, as such, characterised.

We claim:
1. A compound, or salt thereof, of formula (I):

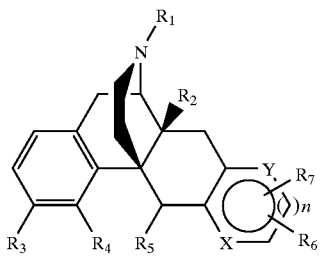

(I)

in which,
R₁ is hydrogen, linear or branched $C_{1-6}$ alkyl, $C_{3-7}$ cycloalkyl, $C_{4-6}$ cycloalkylalkyl, or $C_{3-5}$ alkenyl;
R₂ is hydrogen, hydroxy or $C_{1-5}$ alkoxy;
R₃ is hydrogen, hydroxy, or $C_{1-5}$ alkoxy;
R₄ and R₅, which may be the same or different, are each independently hydrogen, hydroxy, $C_{1-5}$ alkoxy, or together may form an oxy group (—O—);
R₆ is a group C(Z)R₁₂, in which Z is oxygen, R₁₂ is $C_{1-18}$ alkyl, $C_{1-18}$ alkoxy or NR₁₃R₁₄, where R₁₃ and R₁₄, which may be the same or different, are hydrogen, linear or branched $C_{1-6}$ alkyl, benzyl or may form together a $C_{3-6}$ alkyl ring which may be interrupted by an oxygen or a nitrogen; R₇ is hydrogen, or $C_{1-18}$ alkyl,

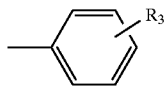

and
n is 0; provided that X and Y are independently NH, or CH or a R₆- or R₇-substituted carbon atom.
2. A compound according to claim 1, in which R₁ is methyl, ethyl, propyl, allyl or cyclopropylmethyl.
3. A compound according to claim 1, in which R₂ is hydrogen or hydroxy.
4. A compound according to claim 1, in which R₃ is hydrogen, hydroxy or methoxy.
5. A compound according to claim 1, in which each of R₄ and R₅ is hydrogen, hydroxy, methoxy or together they form an oxy group.
6. A compound according to claim 1, in which R₆ is COO-iPr, CONEt₂, CONH-i-Pr, CON(i-Pr)₂, CONHCH₂Ph, CON(—CH₂—)₄, CON(—C₂H₄OC₂H₄—) or CON(i-Bu)₂.
7. A compound according to claim 1 in which n=0, X is NH and Y is CH or a R₆- or R₇-substituted carbon atom, where R₆ is a group —C(Z)—R₁₂ where R₁₂ is $C_{1-6}$ alkyl, $C_{1-4}$ alkoxy or NR₁₃R₁₄ where R₁₃ and R₁₄ are as defined in claim 1 and Z is oxygen; and R₇ is methyl.
8. A compound selected from:
[8R-(4bS*,8α,8aβ,12bβ)]-11-Diethylaminocarbonyl-7,10-dimethyl-5,6,7,8,12,12b-hexahydro-4,8-methanobenzofuro[3,2-e]pyrrolo[2,3-g]isoquinoline-1,8a(9H)-diol hydrochloride;
[8R-(4bS*,8α,8aβ,12bβ)]-11-Diethylaminocarbonyl-10-methyl-7-(2-propenyl)-5,6,7,8,12,12b-hexahydro-4,8-methanobenzofuro[3,2-e]pyrrolo[2,3-g]isoquinoline-1,8a(9H)-diol hydrochloride;
[8R-(4bS*,8α,8aβ,12bβ)]-7-Cyclopropylmethyl-11-diethylaminocarbonyl-10-methyl-5,6,7,8,12,12b-hexahydro-4,8-methanobenzofuro[3,2-e]pyrrolo[2,3-g]isoquinoline-1,8a(9H)-diol hydrochloride;
[8R-(4bS*,8α,8aβ,12bβ)]-11-Diethylaminocarbonyl-10-methyl-7-propyl-5,6,7,8,12,12b-hexahydro-4,8-methanobenzofuro[3,2-e]pyrrolo[2,3-g]isoquinoline-1,8a(9H)-diol hydrochloride;
[8R-(4bS*,8α,8aβ,12bβ)]-11-Diisopropylaminocarbonyl-7,10-dimethyl-5,6,7,8,12,12b-hexahydro-4,8-methanobenzofuro[3,2-e]pyrrolo[2,3-g]isoquinoline-1,8a(9H)-diol hydrochloride;
[8R-(4bS*,8α,8aβ,12bβ)]-11-Benzylaminocarbonyl-7,10-dimethyl-5,6,7,8,12,12b-hexahydro-4,8-methanobenzofuro[3,2-e]pyrrolo[2,3-g-]isoquinoline-1,8a(9H)-diol hydrochloride;
[8R-(4bS*,8α,8aβ,12bβ)]-11-Diethylaminocarbonyl-7,10-dimethyl-1methoxy-5,6,7,8,12,12b-hexahydro-(9H)-4,8-methanobenzofuro[3,2-e]pyrrolo[-2,3-g]isoquinoline hydrochloride;
[8R-(4bS*,8α,8aβ,12bβ)]-7,10-Dimethyl-11pyrrolidinocarbonyl-5,6,7,8,12,12b-hexahydro-4,8-methanobenzofuro[3,2-e]pyrrolo[2,3-g]isoquinoline-1(9H)-ol hydrochloride;
[8R-(4bS*,8α,8aβ,12bβ)]-11-Diethylaminocarbonyl-7,10-dimethyl-5,6,7,12,12b-hexahydro-4,8-methanobenzofuro[3,2-e]pyrrolo[2,3-g]isoquinoline-1,8a(9H)-diol hydrochloride;
[8R-(4bS*,8α,8aβ,12bβ)]-7,10-Dimethyl-11-morpholinocarbonyl-5,6,7,8,12,12b-hexahydro-4,8-methanobenzofuro[3,2-e]pyrrolo[2,3-g]isoquinoline-1,8a(9H)-diol hydrochloride;
[10R,4bS-(4bβ,9aβ)]-7-Diisopropylaminocarbonyl-8,14-dimethyl-4-hydroxy-3-methoxy-4b,5,9,9a,10,11-hexahydro-(6H)-[2,3-h]pyrrolo[10,4b]imino ethanophenanthrene (*);
[8R-(4bS*,8α,8aβ,12bβ)]-11-Diisopropylaminocarbonyl-7,10-dimethyl-1-methoxy-5,6,7,8,12,12b-hexahydro-(9H)-4,8-methanobenzofuro[3,2-e]pyrrolo[2,3-g]isoquinoline hydrochloride;
[8R-(4bS*,8α,8aβ,12bβ)]-11-Diethylaminocarbonyl-7,10-dimethyl-1-methoxy-5,6,7,8,12,12b-hexahydro-4,8-methanobenzofuro[3,2-e]pyrrolo[2,3-g]isoquinoline-8a(9H)-ol hydrochloride;
[10R,4bS-(4bβ,9aβ)]-7-Diethylaminocarbonyl-8,14-dimethyl-4-hydroxy-3-methoxy-4b,5,9,9a,10,11-hexahydro-(6H)-[2,3-h]pyrrolo[10,4b]imino ethanophenanthrene(*);
[8R-(4bS*,8α,8aβ,12bβ)]-7,10-Dimethyl-1-methoxy-11-(2-methylpropyl)oxycarbonyl-5,6,7,8,12,12b-hexahydro-[9H]-4,8-methanobenzofuro[3,2-e]pyrrolo[2,3-g]isoquinoline hydrochloride;
[8R-(4bS*,8α,8aβ,12bβ)]-11-Diisobutylaminocarbonyl-7,10-dimethyl-1-methoxy-5,6,7,8,12,12b-hexahydro-[9H]-4,8-methanobenzofuro[3,2-e]pyrrolo[2,3-g]isoquinoline (*);
[8R-(4bS*,8α,8aβ,12bβ)]-7,10-Dimethyl-11-isopropylaminocarbonyl-1-methoxy-5,6,7,8,12,12b-hexahydro-[9H]-4,8-methanobenzofuro[3,2-e]pyrrolo[2,3-g]isoquinoline hydrochloride;
9. A pharmaceutical composition comprising a safe and effective amount of a compound according to claim 1 and a pharmaceutically acceptable carrier.
10. A method for the treatment and/or prophylaxis in mammals of pain, organ transplant or skin graft rejection, allergies, inflammation brain cell destruction, drug and alcohol abuse, excess gastric secretion, diarrhoea, cardiovascular and respiratory diseases, cough and respiratory depression, mental illness, epileptic seizures and other neurologic disorders, which comprises administering to the mammal in need of such treatment and/or prophylaxis an effective amount of a compound according to claim 1.

* * * * *